United States Patent [19]

Seare, Jr.

[11] Patent Number: 5,911,757
[45] Date of Patent: Jun. 15, 1999

[54] METHODS AND APPARATUS FOR TRANSCUTANEOUS ACCESS

[76] Inventor: William J. Seare, Jr., 3190 E. Chula Vista Cir., Salt Lake City, Utah 84121

[21] Appl. No.: 08/478,232

[22] Filed: Jun. 7, 1995

Related U.S. Application Data

[63] Continuation-in-part of application No. 08/324,440, Oct. 17, 1994, abandoned, which is a continuation-in-part of application No. 07/960,004, Oct. 13, 1992, Pat. No. 5,356,429, which is a continuation of application No. 07/701,021, May 16, 1991, abandoned.

[51] Int. Cl.$^6$ .............................. A61F 2/02; A61B 17/00
[52] U.S. Cl. ............................................. 623/11; 604/174
[58] Field of Search .................................. 623/10, 11, 12, 623/1, 8; 604/174, 175

[56] References Cited

U.S. PATENT DOCUMENTS

| | | | |
|---|---|---|---|
| 3,562,820 | 2/1971 | Braun ........................................ | 623/12 |
| 3,577,837 | 5/1971 | Bader, Jr. ................................. | 623/16 |
| 3,783,454 | 1/1974 | Sausse et al. ............................. | 623/12 |
| 3,818,511 | 6/1974 | Goldberg et al. ......................... | 623/12 |
| 4,298,998 | 11/1981 | Naficy ....................................... | 623/8 |
| 4,534,761 | 8/1985 | Raible ....................................... | 623/12 |
| 4,585,458 | 4/1986 | Kurland .................................... | 623/20 |
| 4,597,763 | 7/1986 | Schwikhart ............................... | 623/8 |
| 4,634,443 | 1/1987 | Haber ............................... | 128/DIG. 25 |
| 4,676,795 | 6/1987 | Grundei .................................... | 623/8 |
| 4,685,447 | 8/1987 | Iversen et al. ............................ | 623/8 |
| 4,769,038 | 9/1988 | Bendavid et al. ........................ | 623/13 |
| 4,773,909 | 9/1988 | Chaglassian ............................. | 623/8 |
| 4,790,848 | 12/1988 | Cronin ....................................... | 623/8 |
| 4,850,953 | 7/1989 | Haber et al. ...................... | 128/DIG. 25 |
| 4,936,858 | 6/1990 | O'Keeffe ................................... | 623/8 |
| 4,994,084 | 2/1991 | Brennan .................................... | 623/11 |
| 5,011,494 | 4/1991 | von Recum et al. ..................... | 623/11 |
| 5,033,481 | 7/1991 | Heyler, III ................................ | 623/11 |
| 5,376,117 | 12/1994 | Pinchuk et al. ........................... | 623/11 |
| 5,391,156 | 2/1995 | Hildwein et al. ....................... | 604/174 |

FOREIGN PATENT DOCUMENTS 3609910  10/1987  Germany ............................... 623/11

OTHER PUBLICATIONS

Seare, W.J. Pantalos, G.M., Burns, G,L, Mohammed, F., Olson, D.B.: *Exploration of Use and Advantages of Controlled Porosity Surface Modifications in Materials for Vascular and Cardiovascular Application.* The Proceedings Cardiovascular Science and Technology Conference, Dec. 2–4, 1991, The Association for the Advancement of Medical Instrumentation.

*Primary Examiner*—David J. Isabella

[57] ABSTRACT

The methods and apparatus of the present invention permit stable transcutaneous access. Some preferred embodiments of the invention provide body pocket access channels that provide stable means for communicating between the exterior of the body and a natural or created internal body pocket. Other embodiments involve the inclusion of an attachment elements surrounding a device sought to be passed from a location external of a patient's body to a location within the body at the exit site, but which are attached to the device at a location within the body rather than at the exact location where the device passes through a patient's skin, thereby forming a body pocket that will reduce stress or strain at the exit site. Several alternative embodiments for effecting body pockets through use of attachment elements are disclosed.

18 Claims, 6 Drawing Sheets

METHODS AND APPARATUS FOR TRANSCUTANEOUS ACCESS

RELATED APPLICATIONS

This application is a continuation-in-part of Ser. No. 08/324,440, filed Oct. 17, 1994, now abandoned, incorporated herein by reference, which was a continuation-in-part of Ser. No. 07/960,004, filed Oct. 13, 1992 which issued as U.S. Pat. No. 5,356,429 on Oct. 18, 1994, incorporated herein by reference, which was a continuation of Ser. No. 07/701,021, filed May 16, 1991, now abandoned.

BACKGROUND OF THE INVENTION

1. The Field of the Invention

This invention relates to transcutaneous access, and, more particularly, to methods and apparatus for use in establishing and maintaining stable transcutaneous access.

2. The Relevant Technology

Many medical situations require the establishment of transcutaneous access into a region of a patient's body. Transcutaneous access has been long practiced for numerous medical treatments, and the establishment of stable transcutaneous access has long been the subject of discussion and clinical investigations and treatment. Unfortunately, serious problems frequently occur when attempting to achieve transcutaneous access. Both for short term and chronic access, infection of the access site often results in failure of the device placement. The modes of failure vary from local exit site infections to deeper pocket infections or even more remote infections with continuation of the infection to involve areas distant from the transcutaneous exit site. An example of such implant device failures is exemplified by continuous ambulatory peritoneal dialysis (CAPD) catheters. Many innovations have been instituted to try to eliminate the infections associated with these transcutaneous catheters.

These infections fall into several general categories, although it will be appreciated that these problems are interrelated, and may also be thought of as lying along a continuum. One common problem is manifested as an exit site infection, which involves an infection from the location where the catheter enters the skin to, generally speaking, the location of the first Dacron subcutaneous cuff. This is an area typically from 1.0 cm to 2.5 cm from the surface of the skin where the catheter exits the skin. The next is a tunnel infection, which is an infection involving the first Dacron cuff and along the tunnel of the subcutaneous course of the catheter to or involving the second Dacron cuff, if one is supplied, which is generally located in the rectus abdominus muscle. Another type of infection is peritonitis, which involves the peritoneal space along with the catheter within the peritoneum. It is believed that an exit site infection can proceed to a tunnel infection and subsequently cause peritonitis, demonstrating the interrelationships of these infections. Many efforts have been directed toward reducing the incidence of exit site infection, but little change in exit site infection rates has been observed, despite new advances in cuffing materials, implant techniques and exit site care.

Another example of failure of transcutaneous access has been observed in connection with artificial heart and heart assist lines, where either a transcutaneous access is needed for electrical power and possibly venting, or pneumatic powering of the heart. Here the infection(s) may involve the exit site, proceed along the drive line to the pump pocket where it can involve the entire pocket of the pump and subsequently to the vascular grafts. Even though it is rare for these infections to cause the demise of the patient, they do create significant morbidity and expense associated with treatment, and may require operative intervention.

SUMMARY AND OBJECTS OF THE INVENTION

The problems caused by transcutaneous access are well known, and have presented a significant impediment to many medical procedures. Accordingly, it will be appreciated that it is a primary object of the present invention to provide methods and apparatus permitting stable transcutaneous access to be established and maintained.

Other objects and features of the present invention will become more fully apparent from the following description and appended claims, or may be learned by the practice of the invention as set forth hereinafter.

Stable transcutaneous access may be obtained in accordance with the present invention. It is a feature of the present invention to form a body pocket through which a transcutaneous device passes from an external location to a location within a patient's body.

Certain preferred embodiments of the invention involve the inclusion of an attachment element which forms a body pocket comprising a cushion space which can permit movement of the transcutaneous device or transfer of movement in a manner which minimizes forces applied to the patient's skin at the exit site. Other embodiments utilize an attachment element to form a body pocket closed at the internal end, but unattached to the transcutaneous device at the exact location where the device passes through a patient's skin, again forming a body pocket that will reduce stress and strain applied to the skin at the exit site.

BRIEF DESCRIPTION OF THE DRAWINGS

In order that the manner in which the above-recited and other advantages and objects of the invention are obtained may be understood, a more particular description of the invention briefly described above will be rendered by reference to a specific embodiment thereof which is illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
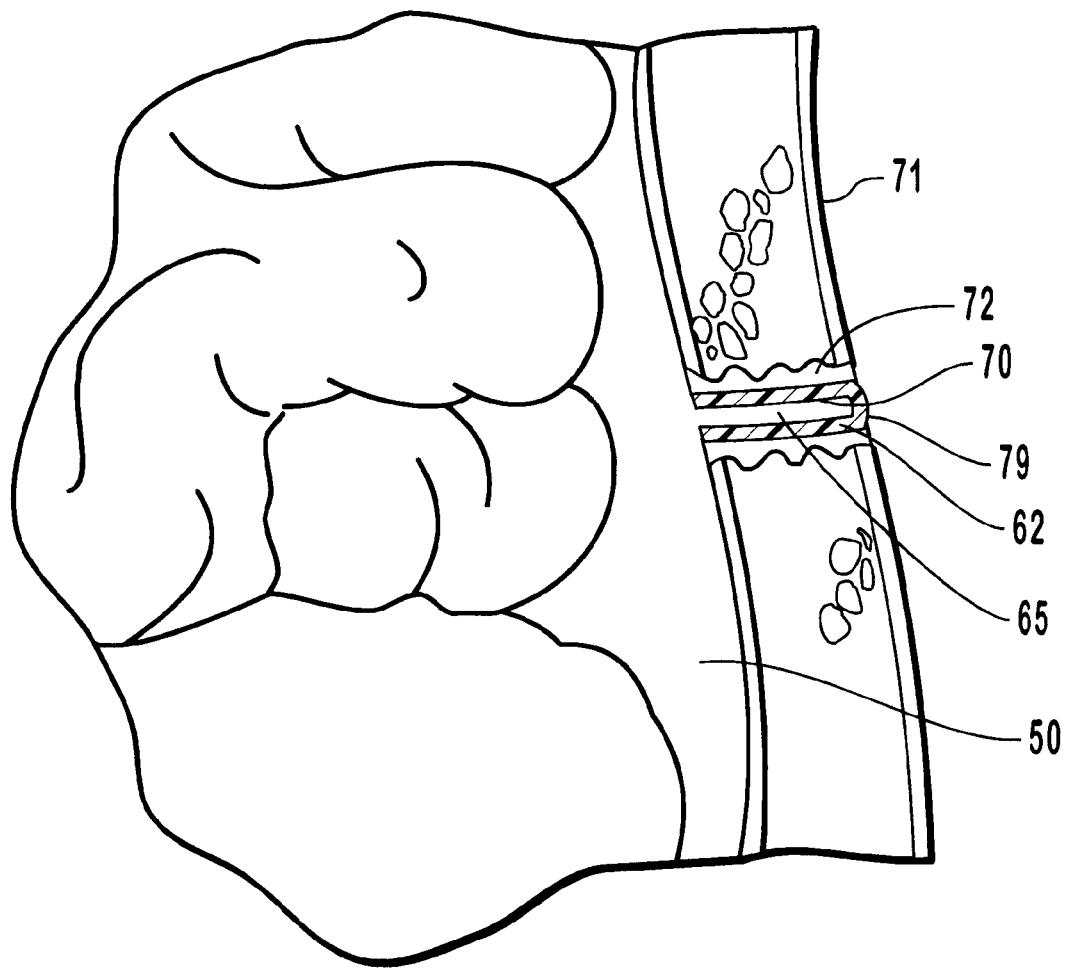
FIG. 1 illustrates a cross-section view of a stable body pocket access channel.

This invention relates to methods and apparatus for establishing and maintaining effective transcutaneous access from a location external of a patient's body to a location within the body.

It was noted above that transcutaneous access frequently fails due to infection of the access site. The modes of failure vary from local exit site infections to deeper pocket infections or even more remote infections with continuation of the infection to involve areas distant from the transcutaneous exit site. These failures appear to fall into five general categories: exit site infections, tunnel infections, peritonitis, pocket infections and distant infections. As explained previously, exit site infections typically involve an infection from the point where a catheter exits the skin to the point where most conventional devices utilize a Dacron subcutaneous cuff. Tunnel infections typically occur in the region along the tunnel of the subcutaneous course of the catheter. Peritonitis involves the peritoneal space. Pocket infections involve the implant capsule into which a device extends. Distant infections can result from a contiguous spread or a hematogenous spread from any of the other types of infections.

From careful examination of hundreds of failed transcutaneous catheter placements, it appears that one significant cause of failure results from microtrauma at the location where conventional transcutaneous devices exit the skin. Such microtrauma appears to result primarily from movement of the device and/or the skin at the exit site. This movement of the device is translated to a force or movement between the skin and catheter which damages the skin and subcutaneous integrity and hence provides an opening for infection.

Any natural or surgically-created body pocket, tissue, organ, or system can be made stably accessible from the outside of the body in accord with the present invention. A suitable biocompatible catheter or other device, including a sheet or sheets of material disclosed in copending application Ser. No. 08/324,440, is provided with tissue ingrowth surfaces as described herein, and then placed through a percutaneous opening. The device is positioned to permit tissue ingrowth from the surrounding tissue surfaces and thereby becomes stably secured in position.

One example of a device utilizing material of the type described in copending application Ser. No. 08/324,440 is shown in cross-section in FIG. 1, wherein either a single sheet or multiple sheets of such material is formed into a tube 62 having an outer tissue-adhering surface 72 and an inner non-adhering surface 70. Tube 62 could be positioned as illustrated to extend from the exterior surface of the skin 71 through the subcutaneous tissue and the rectus muscle and through the peritoneum to the peritoneal cavity 50. The tissue-adhering surface 72 permits tissue ingrowth and thereby stably secures tube 62 in position. In this manner, a stable body pocket is created providing access to the peritoneal cavity 50 from outside of the body.

Tube 62 defines a stable body pocket extending from the exterior surface of the skin 71 to the interior surface of the peritoneum, thereby providing an access channel 65 which connects the peritoneal cavity 50 to the outside environment. The exterior tissue-adhering surface 72 of tube 62 permits tissue ingrowth and thereby becomes securely fixed in place. The natural internal body forces may collapse access channel 65 such that a potential space body pocket is created. Additionally, at the percutaneous opening 79, a cap (not shown) can be placed or an integral valve or port (not shown) can be formed such that addition or removal of fluids or other materials into access channel 65 can be controlled.

One use of such a stable body pocket access tube would be to provide access for a heart assist device or an implanted artificial heart. As shown schematically in cross-section in FIG. 2, a pneumatic drive line, or alternatively a conduit for electric wires and vent tubes, designated by reference numeral 85, could be positioned within the stable body pocket access channel 65 shown in FIG. 1 so as to leave a cushion space 81. The drive line is advantageously smaller in diameter than access channel 65 and is sealed to tube 62 around percutaneous opening 79 and around opening 82 into the peritoneal cavity. This sealing creates a contained cushion space 81 between the outer surface of the pressure line and the inner surface 70 of the tube. An opening 86 to this space provides means for filling the space with fluid, either liquid or gas, or other substances or bioactive materials. For example, an antibiotic solution could be placed into the space such that diffusion across the solid membrane of tube 62 into the ingrown tissue of outer tissue adhering surface 72 could occur. The cushion space 81 thereby provides a flexible cushion and space permitting some movement of the pressure line 85 within tube 62 while still maintaining enough pressure to keep the outer surface 72 of tube 62 in contact with the ingrown surrounding tissue.

Figure 2:
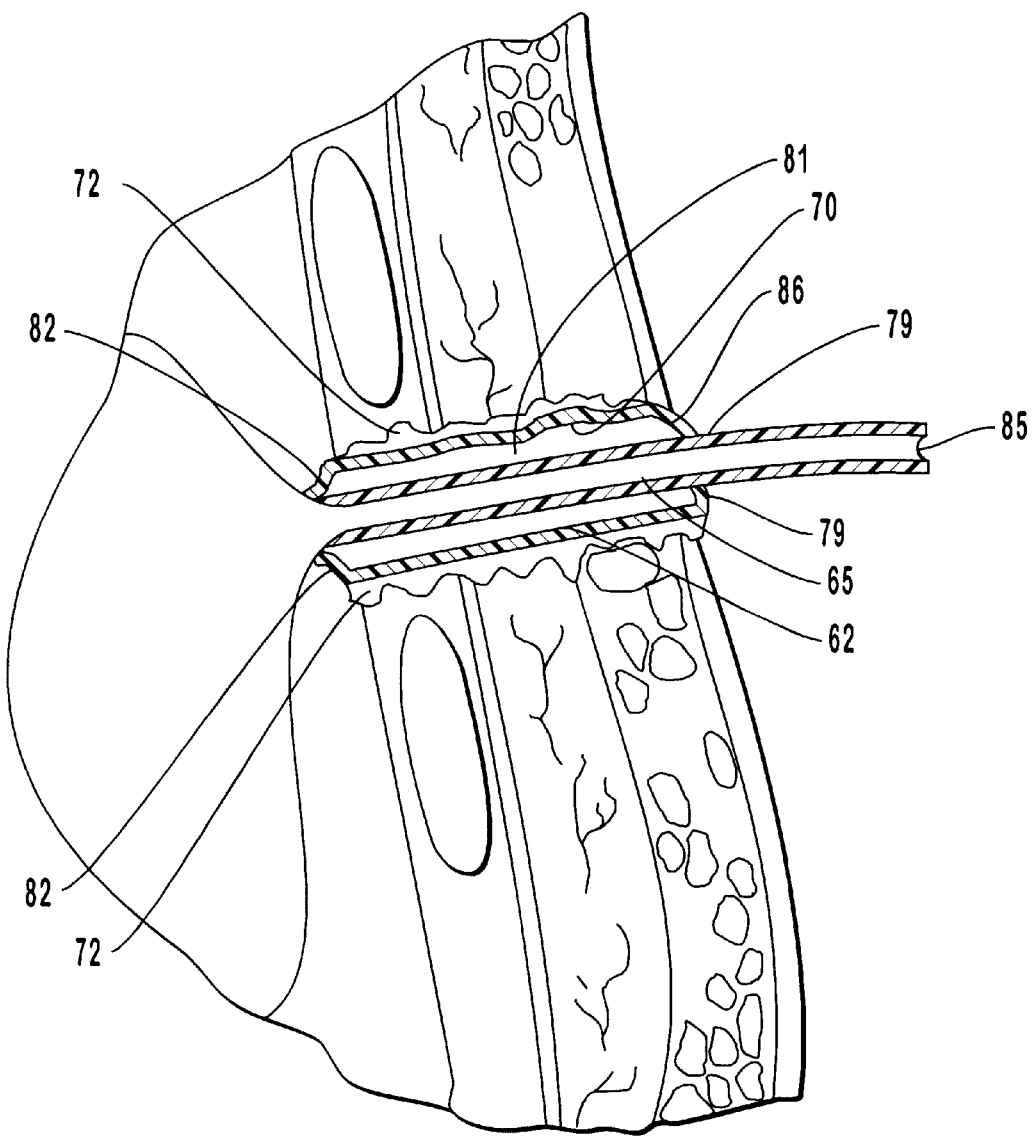
FIG. 2 illustrates a cross-section view of a stable body pocket access channel containing a drive line or vent tube.
Figure 3:
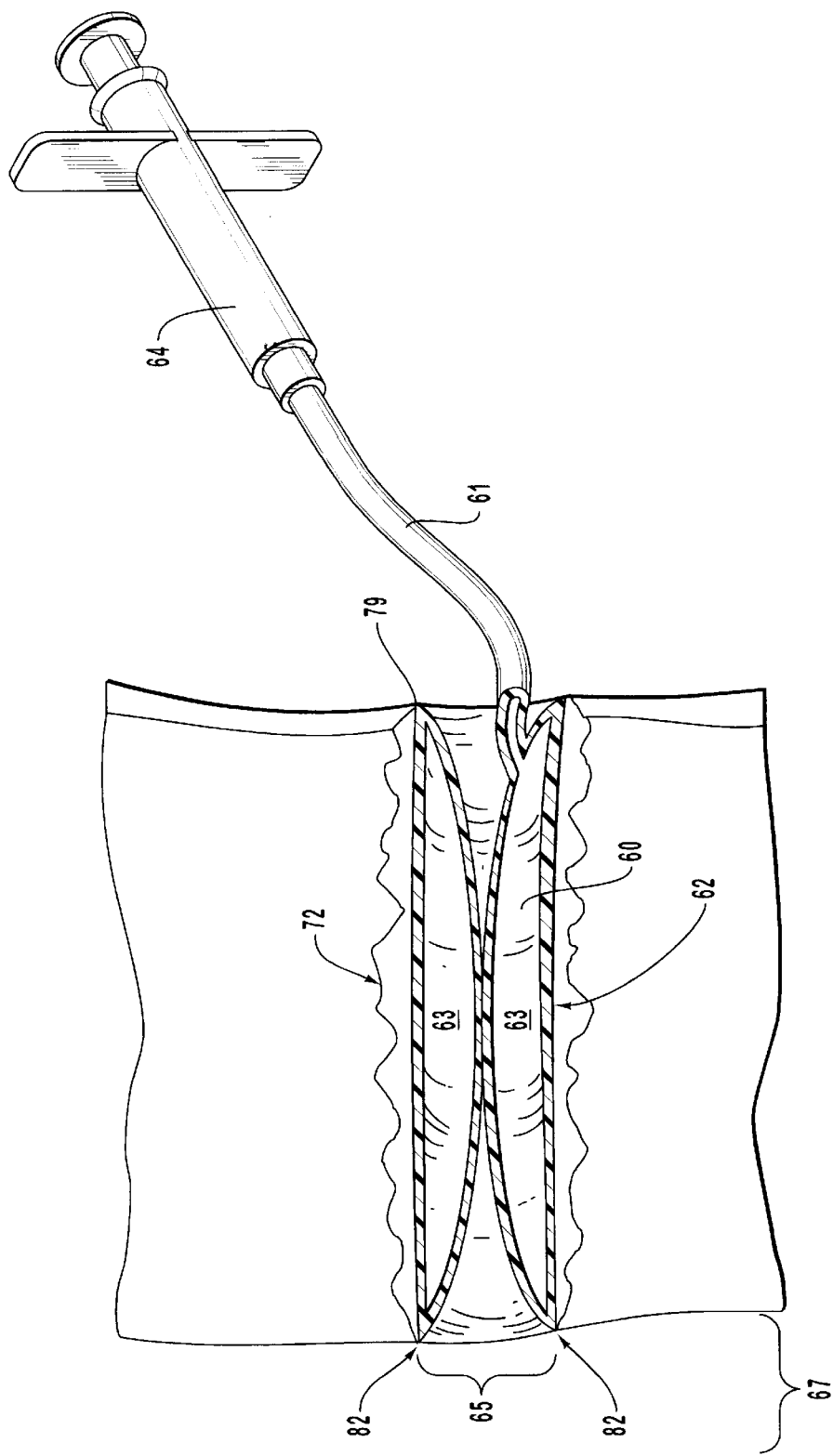
FIG. 3 illustrates a cross-section view of a stable body pocket access channel containing a balloon tube.

A stable body pocket access tube as shown in cross-section in FIG. 1 could also be used to contain a balloon type apparatus to provide control of access through the tube. An example of an embodiment comprising a collapsible balloon tube positioned within the access tube is shown in FIG. 3. The balloon tube 60 is formed of a flexible biocompatible sheet material having non-adhering surfaces. The balloon tube 60 is of a smaller diameter than tube 62 and is positioned within tube 62. The balloon tube 60 is connected to tube 62 such that a continuous inflatable space 63 is formed between the outer surface of the balloon tube and the inner surface of tube 62. For example, as shown in FIG. 3, the balloon tube 60 is joined to tube 62 at or near the percutaneous opening 79 and at or near the opening 82 into the peritoneal cavity, or any intermediate positions.

The sheet material for forming the access channel tube and the balloon tube can be any suitable material which can contain the desired fluid, gas or other desired material. The sheet material can be either permeable, semi-permeable, or non-permeable depending on the desired volume of the inflatable space and the desired leakage through the sheets into the tissue ingrowing at the outer surface 72 of tube 62 or into access channel 65 through balloon tube 60. The inflatable space 63 can then be inflated or deflated with a gas, such as nitrogen or carbon dioxide or room air, or a liquid such as normal saline or sterile water, with or without additives such as antibiotics. Fluid can be added to or withdrawn from the inflatable space 63 either by needle puncture, or by a tube 61, positioned to provide access from outside the body to the inflatable space 63, connected to a syringe 64. In this manner, fine adjustment of the volume within inflatable space 63 can be achieved. Adjustment of the volume within inflatable space 63 controls the opening through tube 62 thereby permitting control of access between the peritoneal space 67 and the outside environment.

It should be understood that the inflatable space could be divided into two or more separate inflatable spaces thereby permitting separate control of volumes within the inflatable spaces at various points along access channel 65. A stable body pocket access channel containing one or more inflatable spaces could be utilized for various purposes.

For example, a stable body pocket access channel containing a balloon tube as shown in FIG. 3 could be used for peritoneal dialysis. The inflatable space is filled with normal saline to an appropriate volume to keep the outside environment from entering the access channel. An antibacterial substance, such as dilute iodophor solution, can be included in the normal saline. The solution can diffuse across the balloon tube membrane in either direction. Specifically, the solution can diffuse into the access channel lumen or into the tissue surrounding the tube 62 to reduce bacterial or bacterial biofilm growth. In this manner, the balloon tube acts as a drug delivery system.

When peritoneal dialysis is desired, the balloon tube is deflated to the desired volume to just allow insertion of a single catheter from the outside of the body to the peritoneal space. The volume may be readjusted to hold the catheter in position. Dialysis fluids can then be introduced into the peritoneal space, the catheter removed, and the balloon reinflated. The dialysis fluid, or any other desired fluid such as, for example, solutions of antibiotics, chemotherapeutic agents, or other such bioactive material, is allowed to contact the peritoneal contents for a selected period of time known as the dwell time. The balloon tube can then be partially or totally deflated so that additional catheters may be inserted or removed as desired. The cycle can be immediately repeated or any desired combination of dialysis fluid, balloon fluid, or catheter introduction or removal can be instituted. In this manner, the need to use flanges, cuffs, or other fixation devices to secure the pocket maintaining device to the skin, peritoneum, muscle or subcutaneous tissue is reduced. However, if desired, a subcutaneous skin cuff and/or a pre-peritoneal or rectus muscle cuff can be formed by extending the tissue-adhering surface of the sheet forming tube 62 such that tissue ingrowth into the surrounding tissue occurs. In this manner, the tube is even more securely fixed in position.

Figure 4:
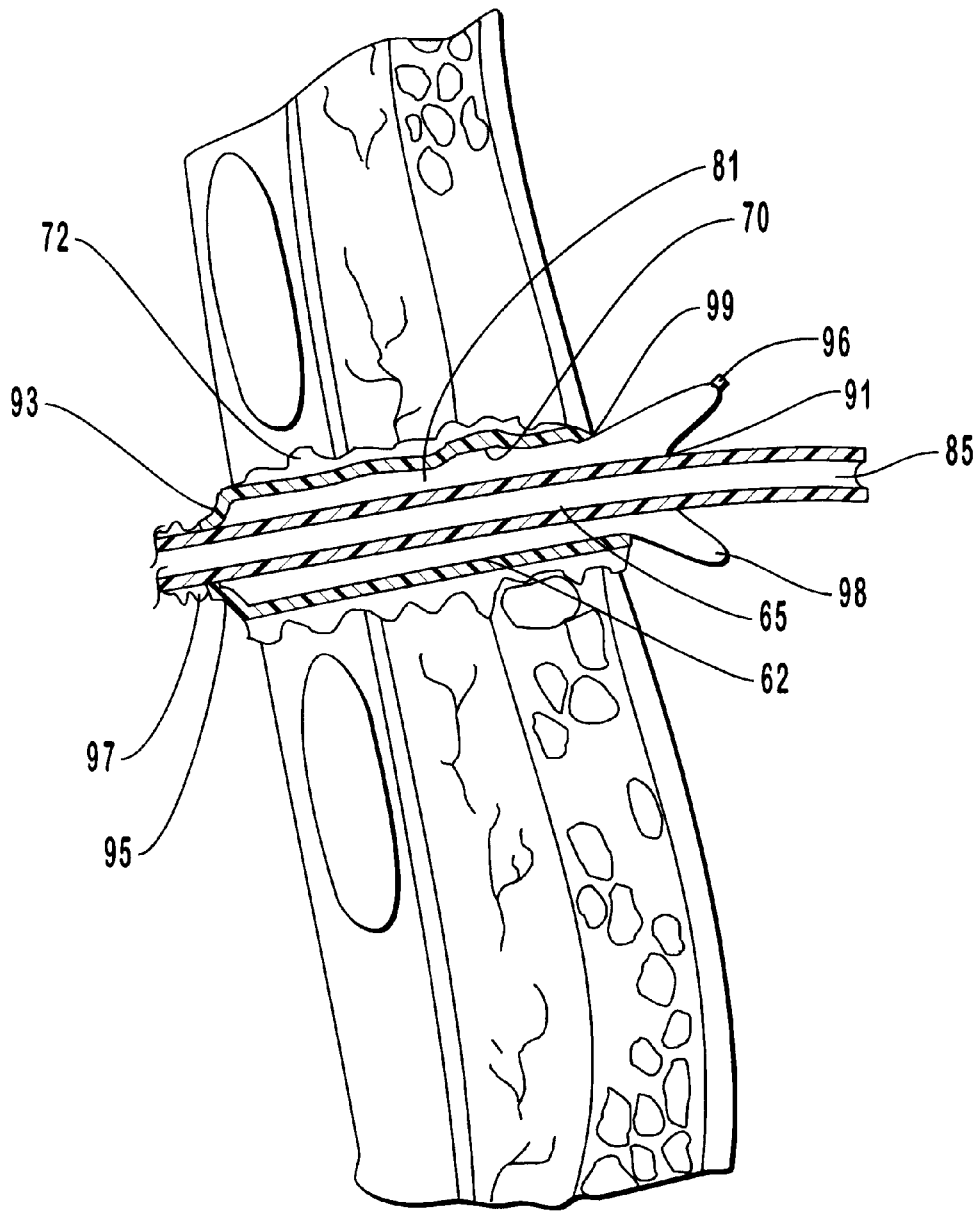
FIG. 4 illustrates in cross-section the establishment of a stable transcutaneous access including a balloon extending outside the patient's body, with a tube coursing therethrough.

In another embodiment of the present invention, illustrated schematically in FIG. 4, a body pocket access tube can be established for use in placement of any transcutaneous device. For purposes of discussion, this embodiment is described in connection with a heart assist application. Thus, as shown schematically in cross section in FIG. 4, a pressure line 85 may be advantageously positioned within a stable body pocket access channel 65. For convenience of illustration, only the portion of the pressure line passing through the skin is illustrated in FIG. 4, and it should be understood that both ends of the transcutaneous device extend further in order to complete its function.

The pressure line 85 is preferred to be sized smaller in diameter than access channel 65 and is sealed to the access channel in two places, depicted by reference numerals 91 and 93. This seal creates a body pocket which shall be referred to in connection with FIG. 4 as cushion space 81 located between the outer surface of the pressure line and the inner surface 70 of the tube. An optional opening 96 to this space provides means for filling the space with fluid, either liquid or gas, or other substances or bioactive material. For example, an antibiotic solution can be placed into the space such that diffusion into the surrounding tissue will occur. The cushion space 81 thereby provides a flexible cushion permitting movement of the pressure line 85 within the inner surface 70 of the tube while still maintaining enough pressure to keep the outer surface 72 of the tube 62 in contact with the ingrown surrounding tissue.

In addition, the attachments of the inner tube 85 to the outer tube 62 at locations 93 and 91 are different. They are constructed in such a manner that the length of the tube section 93 which attaches and seals the two tubes 85 and 62 together is shorter in total length than is the outer tube 98 which seals the two tubes 85 and 62 on the outside. In constructing the sealing tubes or sections 93 and 98 in such a fashion, the movement and stresses which may develop from normal activities and manipulations required by the patient are minimized at the specific skin junction attachment 99 by the accordion effect of the redundancy of the attachment of the two tubes. In this construction it is difficult for microtrauma, compression or tension failure to develop at the ingrown tissue-implant interface of the prosthesis. Further, by pressurizing the sealed cushion space with fluid, such as air, water, saline, gels or other substances, the tendency for the ingrown epidermis, dermis and immediate subcutaneous tissue to pull loose can be additionally minimized. Hence, it will be seen that this structure cooperates to form an attachment element for the pressure line which forms a body pocket that reduces stress at the body exit site. Alternatively, it should be understood that section 93 could have a stiffer compliance than section 98 to accomplish a similar stress relief.

As discussed previously, it should be understood that the inflatable space could be divided into two or more separate inflatable spaces thereby permitting separate controls of the volumes within the inflatable spaces and therefore the pressures at various points along tube 62 and its ingrown parts 72. It should also be understood that the porous outer surface 72 of the tube 62 may become intimately attached to the outer surface of tube 85 as shown at 97 where the advantages of tissue ingrowth may continue. It is not necessary that the porous material comprising 72 will be the same as the porous material of 97.

A preferred porous surface for apparatus in accord with the present invention is the porous material described in copending application Ser. No. 08/156,675, but may also be formed of another material that accomplishes tissue fixation, as described elsewhere herein. Extending the porous material some distance beyond location 95 may permit more effective dispersal of the stresses of catheter movement or pistoning by distributing those stresses along the relatively more fixed section represented at 97 and to a lesser degree to the tissue grown into 72. Minimal pistoning or tension forces should be transmitted to the actual implant-skin interface at 99.

Figure 5:
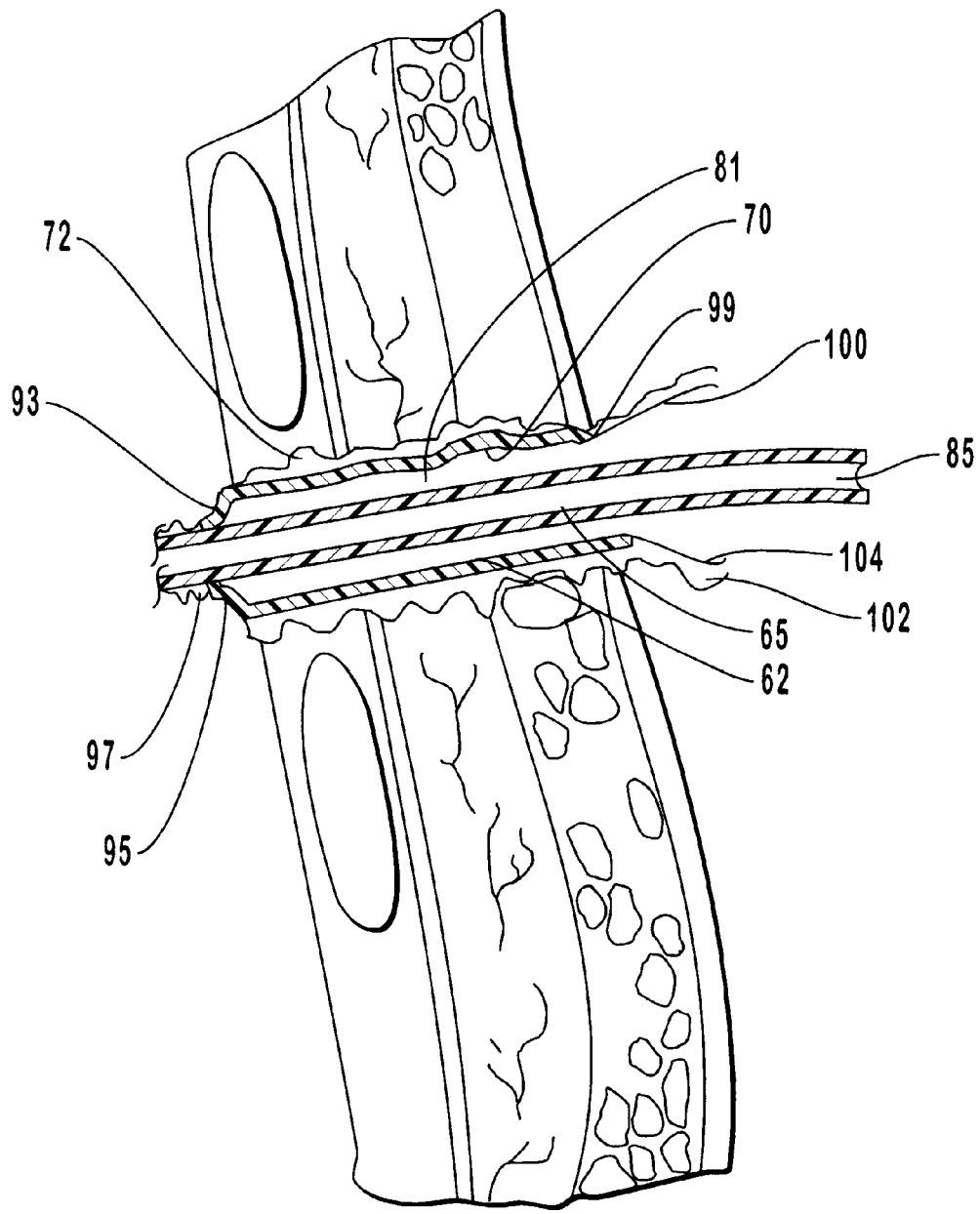
FIG. 5 illustrates in cross-section yet another embodiment of the present invention, this embodiment showing stable access to outside the patient's body.

In another embodiment of the present invention, represented schematically in FIG. 5, the porous section 72 which is ingrown by tissue may be extended continuously to the outside of the body past the skin-implant junction at 99 for some distance, as indicated by reference numeral 102. The section to the outside of 99 will allow for the final settling of position and tissue ingrowth of the porous section 72 within the body, so that it is not critical at surgical implantation that the porous-non-porous junction be precisely established and maintained at 99. Alternatively, the porous material may terminate at the exact location desired to be connected at 99 (not shown).

It should be noted that a feature of the embodiment of FIG. 5 is the lack of any attachment of tube 62 to pressure line 85 at the location where the pressure line passes the exit site into the patient's body. By comparison to FIG. 4, the embodiment of FIG. 5 lacks a seal 91. Line 85 is secured to tube 62 at a location internal to the patient, however, as indicated by numeral 93. This arrangement advantageously avoids the primary stress forces caused by movement of line 85 away from the skin at the exit site, such as might be observed with the embodiment like FIG. 2. Hence, it will be appreciated that the embodiment of FIG. 5 substantially reduces trauma to the skin at the exit site. It will be appreciated that this aforementioned structure cooperates to form an attachment element for the pressure line which forms a body pocket 81 that reduces stress at the body exit site.

In the use of the embodiment of FIG. 5, attachment of body tissues to outer tissue adhering surface 72 will occur quickly, and a stable tissue-porous implant interface will occur along surface 72 and will be established at a time anywhere from a few minutes due to fibrin or serum or tissue adhesion, to several days or weeks as tissue ingrowth occurs. At an appropriate time, the porous section to the outside of 99 may be trimmed from the non-porous section 104 so that the sponge effect of the porous section with its attendant microbiological burden can be reduced or eliminated. It is anticipated that this implantation procedure with the porous portion extending to the exterior with subsequent trimming of the porous portion could be applied to the device proposed in FIG. 4.

Similarly, the entire porous section 102 and non-porous section 104 may be cut just above, at or slightly below the skin-implant junction 99. In practice, the latter is much more easily accomplished than precisely removing the porous section 102 from the non-porous section 104. Furthermore it is anticipated that like in the completely sealed version previously discussed, fluids such as saline or sterile water may be added to the space 81 directly from the outside where they would act to lubricate the opposing surfaces 70 and 106, where 106 represents the outer surface of tube 85, to thereby reduce the microtrauma, shearing and compressive and tensile stresses which might tend to disrupt the tissue-porous implant interface along 72 from 95 to 99 or disrupt the skin-porous implant interface at 99.

Pharmacoactive substances may be added to said lubricant to additionally assist in preventing the establishment, holding under control or destroying bacteria or bacteria produced biofilm complexes from forming along the porous implant-tissue interface 73.

The longer the distance from 99 to 95, the greater the distance over which these aforementioned advantages of stress relief at the skin and subcutaneous tissue, antimicrobial effects can be applied. This will vary with factors depending on the intended use, the diameter of tube 85, the stiffness of tubes 85 and 62, the total length of the catheter, the tissue and location on the body that the tubes are implanted, as well as other factors which will be apparent in light of the teachings herein.

The device can start to have an effect with invagination of the cushion space 81 of less than a millimeter for very small catheters. The space 81 may alternately continue until the entire device is surrounded as described previously for the heart assist device.

Figure 6:
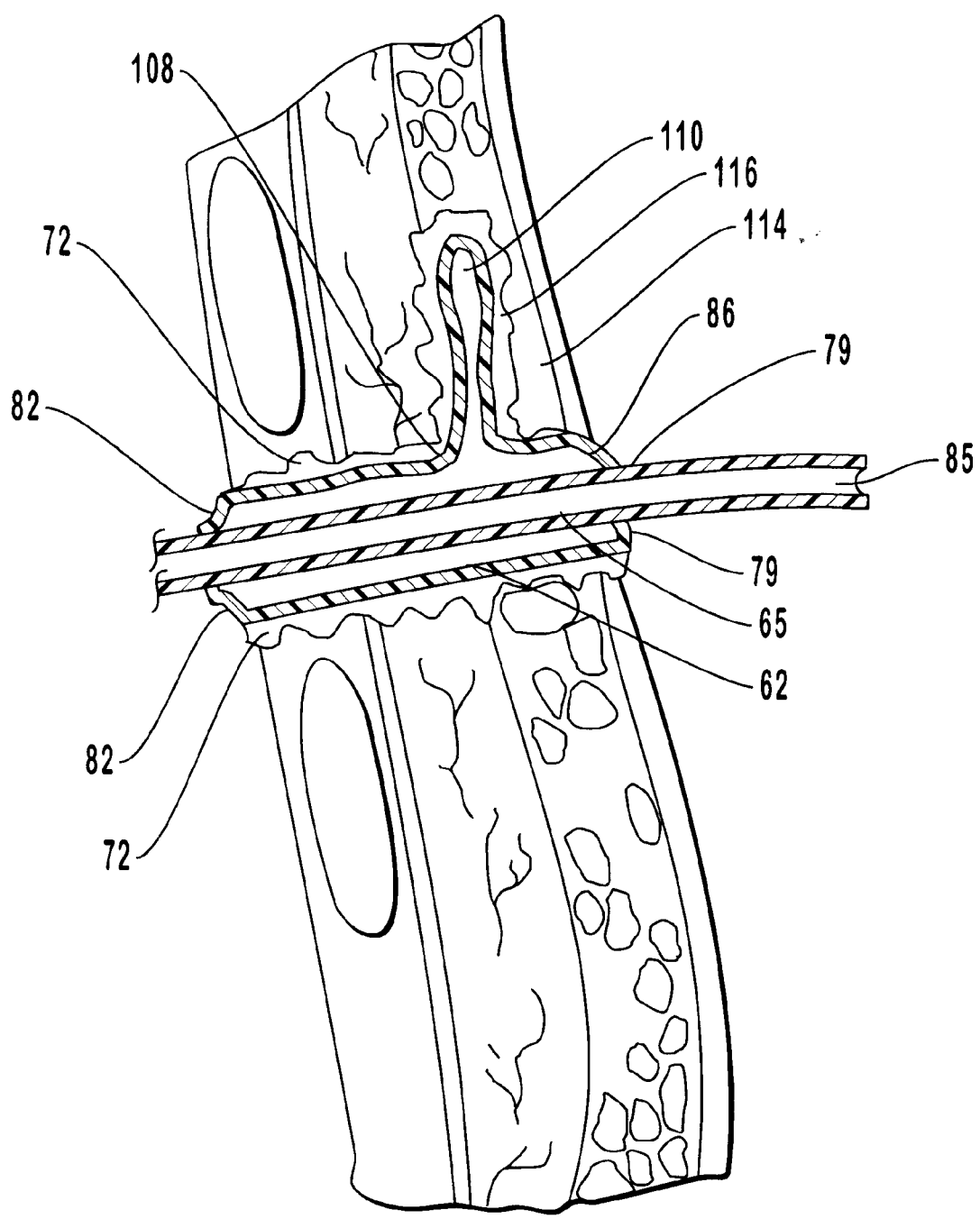
FIG. 6 illustrates in cross-section an embodiment providing stable transcutaneous access in which a body pocket diverges from a tube passing into the patient's body.

In another embodiment of the present invention, represented schematically in FIG. 6, outside tube 62 does not necessarily conform to the shape of tube 85 along its entire length. Tube 62 may diverge from tube 85, such as depicted at 108, creating an additional body pocket 110 as seen in FIG. 6. With this implantable configuration, unlike the use of collars, buttons, flanges and discs applied to transcutaneous implants which really serve to restrict and fix the movement of the overlying skin, this configuration enhances the movement of the overlying skin 114, so that disruption of the skin-implant interface at 99 is even less likely, further minimizing the chance of infection.

In this embodiment, it is advantageous to use a porous material on the tissue contacting surface on this additional body pocket 110 and especially on the superior porous surface which creates vascularity and prevents fibrosis, with healthy tissue ingrowth. In this way, skin flap 114 can be better vascularized and the integrity of the implant-tissue interface can be better maintained. The presently preferred surface comprises an open-cell porous surface of the type described in copending application Ser. No. 08/156,675 filed Nov. 22, 1993, incorporated herein by reference, a continuation of Ser. No. 07/779,387 filed Oct. 18, 1991, now abandoned. This type of surface has been discovered to promote tissue ingrowth of a particularly high quality. This "high quality" tissue ingrowth has advantages beyond merely permitting adherence to a tissue surface. The high quality tissue is vascularized and provides a more advantageous environment than the generally poorly vascularized, fibrous tissue ingrowth generated by other types of surface/tissue interfaces.

The shape of the body pocket 116 is not critical. It may be flat and opposed as in FIG. 6, or it may be more oval and round. It is also anticipated that this configuration may be sealed at the exterior similar to the configuration seen in FIG. 4, and provided with an access for filling 96.

For a CAPD catheter, any of the configurations may be used and each are helpful in their own way. The depth of the invagination of the body pocket 81 may not only extend into the subcutaneous tissue, but on to or through the rectus muscle and on into the peritoneum. For a blood access catheter, the invagination of the body pocket may extend just beneath the skin, or may be constructed to extend up to the introduction of the tube 85 into the vessel itself. Alternately, a very tortuous path may be constructed so that the device doesn't proceed directly from the skin-implant introduction site 99 to the vessel. Additionally, it could be constructed and implanted to course through muscle to obtain additional infection resistance that the vascularity of muscle tissue imparts.

In addition to the use of Dacron and the material described in copending application Ser. No. 08/156,675, various other types of surfaces permit tissue ingrowth at a tissue surface interface. Examples of other types of materials include porous polyurethane and expanded polytetrafluroethylene. The surface architecture which permits tissue ingrowth can comprise a textured, fabric, or porous surface. For example, a foamed silicone porous surface, or sintered or spun porous materials could be used. Fabrics such as dacron felt, velours, or fabric weaves could be used. Textured surfaces such as are formed by salt impregnation and dissolution or are formed by known molding, casting, or flowing procedures to create irregular surfaces could be used.

The present invention may be embodied in other specific forms without departing from its spirit or essential characteristics. It is to be understood and appreciated from the general and specific teachings herein that the devices proposed in FIGS. 1–6 are not meant to be limited to any specific body area, skin entry site or transcutaneous implant application. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for effecting stable transcutaneous access comprising:
 a) at least one biocompatible sheet configured to provide a transcutaneous access channel within a patient's body, said sheet formed into a tube and including:
  i) an outer tissue-adhering surface which promotes tissue ingrowth to thereby secure the sheet in contact with a selected tissue surface, and ii) an inner non-adhering surface which does not permit tissue ingrowth;

wherein said tube has a length suitable for placement within the body of a patient such that said tube is capable of extending from the exterior of the surface of the patient's skin through the subcutaneous tissue of the patient, said tube further having a first open end for providing a percutaneous opening into the body and a second open end for providing access into an internal body space: and b) a transcutaneous access device capable of being circumscribed by said biocompatible sheet such that a body pocket cushion space is formed between said access device and said inner non-adhering surface of said sheet, said body pocket cushion space capable of reducing stress to the tissue at a the location where said access device exits the skin of the patient.

2. An apparatus as recited in claim 1, wherein said transcutaneous access device is affixed to said tube at at least one of said first open end or said second open end.

3. An apparatus as recited in claim 1, wherein said transcutaneous access device is affixed to said tube at said second open end but not at said first open end thereby avoiding the primary stress forces caused by movement of the transcutaneous access device away from the skin at the location where the device exits the patient's skin.

4. A method for effecting stable transcutaneous access, comprising the steps of:
    a) providing at least one biocompatible sheet comprising an outer tissue-adhering surface and an inner non-adhering surface, said sheet being formed into a tube;
    b) placing said tube within the body of a patient such that said tube extends from a location external of a patient's body to a location within the body, said tube further being positioned such that said tissue-adhering surface is in contact with a tissue surface at a location in the body where said tube is desired to be secured by tissue ingrowth;
    c) positioning a transcutaneous access device within said tube such that the access device extends through said tube from a location external of a patient's body to a location within the body, wherein a body pocket cushion space is formed between said access device and said inner non-adhering surface, said body pocket cushion space reducing stress to tissue at the location where said access device exits the body of the patient; and
    d) permitting tissue to adhere to said tissue-adhering surface to thereby stabilize transcutaneous access through said tube.

5. A method as recited in claim 4, wherein the tube has a first open end providing a percutaneous opening into the body and a second open end providing access into an internal body space.

6. A method as recited in claim 5, further comprising the step of affixing the access device to the tube at at least one of said first open end or said second open end.

7. An apparatus for effecting stable transcutaneous access comprising:
    a) at least one biocompatible sheet configured to provide a transcutaneous access channel within a patient's body, said sheet formed into a tube and including:
        i) an outer tissue-adhering surface which promotes tissue ingrowth to thereby secure the sheet in contact with a selected tissue surface, and
        ii) an inner non-adhering surface which does not permit tissue ingrowth; and
    b) a transcutaneous access device capable of being circumscribed by said biocompatible sheet such that a body pocket cushion space is formed between said access device and said inner non-adhering surface of said sheet, said body pocket cushion space capable of reducing stress to the tissue at a location where said access device exits the skin of the patient, wherein said tube further comprises an inlet for providing fluid communication between a location outside of the body and within said body pocket cushion space thereby permitting said body pocket cushion space to be filled with a selected material.

8. An apparatus for effecting stable transcutaneous access comprising:
    a) at least one biocompatible sheet configured to provide a transcutaneous access channel within a patient's body, said sheet formed into a tube and including:
        i) an outer tissue-adhering surface which promotes tissue ingrowth to thereby secure the sheet in contact with a selected tissue surface, and
        ii) an inner non-adhering surface which does not permit tissue ingrowth; and
    b) a transcutaneous access device capable of being circumscribed by said biocompatible sheet such that a body pocket cushion space is formed between said access device and said inner non-adhering surface of said sheet, said body pocket cushion space capable of reducing stress to the tissue at a location where said access device exits the skin of the patient, wherein said access device includes at least one reversibly inflatable balloon.

9. An apparatus as recited in claim 8, wherein adjustment of the volume within said balloon permits control of transcutaneous access through said tube.

10. An apparatus as recited in claim 8, wherein said balloon is formed of selectively permeable material such that selected substances can be inserted into and permitted to diffuse through said balloon.

11. An apparatus for effecting stable transcutaneous access comprising:
    a) at least one biocompatible sheet configured to provide a transcutaneous access channel within a patient's body, said sheet including:
        i) an outer tissue-adhering surface which promotes tissue ingrowth to thereby secure the sheet in contact with a selected tissue surface, and
        ii) an inner non-adhering surface which does not permit tissue ingrowth; and
    b) a transcutaneous access device capable of being circumscribed by said biocompatible sheet such that a body pocket cushion space is formed between said access device and said inner non-adhering surface of said sheet, said body pocket cushion space capable of reducing stress to the tissue at a location where said access device exits the skin of the patient, wherein said access device is a pressure line.

12. An apparatus as recited in claim 11, wherein said biocompatible sheet is formed into a tube.

13. An apparatus for effecting stable transcutaneous access comprising:
    a) at least one biocompatible sheet configured to provide a transcutaneous access channel within a patient's body, said sheet including:
        i) an outer tissue-adhering surface which promotes tissue ingrowth to thereby secure the sheet in contact with a selected tissue surface, and ii) an inner non-adhering surface which does not permit tissue ingrowth; and b) a transcutaneous access device capable of being circumscribed by said biocompatible sheet such that a body pocket cushion space is formed between said access device and said inner non-adhering surface of said sheet, said body pocket cushion space capable of reducing stress to the tissue at a location where said access device exits the skin of the patient, wherein said access device is a pneumatic drive line.

14. An apparatus as recited in claim 13, wherein said biocompatible sheet is formed into a tube.

15. An apparatus for effecting stable transcutaneous access comprising:

a) at least one biocompatible sheet configured to provide a transcutaneous access channel within a patient's body, said sheet including:
   i) an outer tissue-adhering surface which promotes tissue ingrowth to thereby secure the sheet in contact with a selected tissue surface, and
   ii) an inner non-adhering surface which does not permit tissue ingrowth; and b) a transcutaneous access device capable of being circumscribed by said biocompatible sheet such that a body pocket cushion space is formed between said access device and said inner non-adhering surface of said sheet, said body pocket cushion space capable of reducing stress to the tissue at a location where said access device exits the skin of the patient, wherein said access device is a heart assist device.

16. An apparatus as recited in claim 15, wherein said biocompatible sheet is formed into a tube.

17. An apparatus for effecting stable transcutaneous access comprising:

a) at least one biocompatible sheet configured to provide a transcutaneous access channel within a patient's body, said sheet including:
   i) an outer tissue-adhering surface which promotes tissue ingrowth to thereby secure the sheet in contact with a selected tissue surface, and
   ii) an inner non-adhering surface which does not permit tissue ingrowth; and b) a transcutaneous access device capable of being circumscribed by said biocompatible sheet such that a body pocket cushion space is formed between said access device and said inner non-adhering surface of said sheet, said body pocket cushion space capable of reducing stress to the tissue at a location where said access device exits the skin of the patient, wherein said access device is a vent tube.

18. An apparatus as recited in claim 17, wherein said biocompatible sheet is formed into a tube.

* * * * *

UNITED STATES PATENT AND TRADEMARK OFFICE
CERTIFICATE OF CORRECTION

PATENT NO.   : 5,911,757

DATED        : Jun. 15, 1999

INVENTOR(S)  : William J. Seare, Jr.,

It is certified that error appears in the above-identified patent and that said Letters Patent is hereby corrected as shown below:

Cover Page, References Cited, left column, line 8, change "Schwikhart" to --Schweikhart--

Cover Page, Other Publications, please insert the following:

Seare, W.J., Pantalos, G.M., Burns, G.L., Mohammed, F., Olson, D.B.: *The Use of Controlled Porosity Surface Modifications in Artificial Heart Applications.* The Proceedings Cariovascular Science and Technology Conference, page 9, December 12-14, 1992, The Association for the Advancement of Medical Instrumentation.

Seare, W.J., Pantalos, G.M., Burns, G.L., Burt, W.R., Olson, D.B.: *Quantitative Bacterial Analysis of Porous and Smooth Implants and Tissue Interfaces in a 169 Day Pneumatic Total Artificial Heart.* 1993 Abstracts, page 12, 39th Annual Meeting, ASAIO April 29, 30 & May 1, 1993.

Seare, W.J., Pantalos, G.M., Burns, G.L., Burt, W.R., Olson, D.B.: *Quantitative Bacterial Analysis of Porous, Fabric, and Smooth Non-Blood Contacting Implant Surfaces and Their Tissue Interfaces in a 169 Day Pneumatic Total Artificial Heart Animal Recipient,* ASAIO Journal 1993; 39; M668-M647.

Lefton, K. C.: *Fighting Infection With New Technology Applied to Catheters,* Issues in Infection Control, Nephrology News & Issues, Feb. 1995; p. 18-19.

UNITED STATES PATENT AND TRADEMARK OFFICE
CERTIFICATE OF CORRECTION

PATENT NO. : 5,911,757
DATED : Jun. 15, 1999
INVENTOR(S) : William J. Seare, Jr.

It is certified that error appears in the above-identified patent and that said Letters Patent is hereby corrected as shown below:

Cover Page, Abstract, line 7, after "attachment" change "elements" to --element--

Col. 8, line 41, after "surfaces" change "such as" to --which--

Col. 9, line 15, after "at a" delete "the"

Claim 35 (renumbered as Claim 19) as follows:
An apparatus as defined in Claim 1, wherein said tissue adhering surface comprises an open-cell configuration with pore sizes ranging from about 20 to about 1000 microns in size.

Signed and Sealed this

Fifteenth Day of August, 2000

Attest:

Q. TODD DICKINSON

Attesting Officer

Director of Patents and Trademarks